US006677159B1

(12) United States Patent
Mallow

(10) Patent No.: US 6,677,159 B1
(45) Date of Patent: *Jan. 13, 2004

(54) REVERSIBLE DETECTOR FOR GASEOUS CARBON DIOXIDE

(75) Inventor: William A. Mallow, Helotes, TX (US)

(73) Assignee: Southwest Research Institute, San Antonio, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/735,292

(22) Filed: Dec. 2, 1998

Related U.S. Application Data

(63) Continuation-in-part of application No. 08/617,537, filed on Mar. 15, 1996, now abandoned, which is a continuation-in-part of application No. 08/422,002, filed on Apr. 12, 1995, now abandoned, which is a continuation-in-part of application No. 07/919,788, filed on Jul. 24, 1992, now Pat. No. 5,322,797, which is a continuation of application No. 07/534,198, filed on Jun. 6, 1990, now Pat. No. 5,183,763.

(51) Int. Cl.[7] .......................... G01N 33/497; A62B 9/06
(52) U.S. Cl. ................. 436/133; 436/169; 128/207.14; 422/57; 422/61
(58) Field of Search .................. 436/169, 133, 436/167; 128/207.14; 422/57, 61

(56) References Cited

U.S. PATENT DOCUMENTS

| | | | | | |
|---|---|---|---|---|---|
| 4,928,687 | A | * | 5/1990 | Lampotang et al. | 128/207.14 |
| 4,994,117 | A | * | 2/1991 | Fehder | 436/133 |
| 5,178,831 | A | * | 1/1993 | Sakota et al. | 422/56 |
| 5,183,763 | A | * | 2/1993 | Mallow et al. | 436/106 |
| 5,322,797 | A | * | 6/1994 | Mallow et al. | 436/106 |
| 5,846,836 | A | * | 12/1998 | Mallow | 436/169 |

* cited by examiner

Primary Examiner—Lyle A. Alexander
(74) Attorney, Agent, or Firm—Paula D. Morris & Associates, P.C.

(57) ABSTRACT

An apparatus and method for visually and continuously monitoring gaseous concentrations of electrophiles such as carbon dioxide. A coating composition comprising an organic binder, filler/pigment, an activator, and carbon dioxide sensitive color indicator interacts with a primed substrate to which it is applied for support. The coated primed substrate may then be used for estimation of carbon dioxide concentration by the detection of a substantially instantaneous and reversible color change of the coated primed substrate.

31 Claims, 1 Drawing Sheet

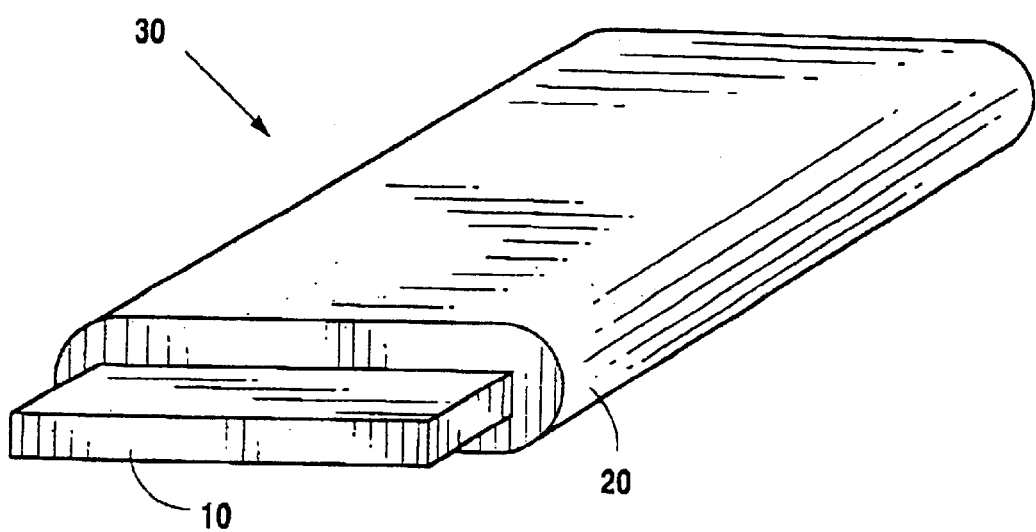

REVERSIBLE DETECTOR FOR GASEOUS CARBON DIOXIDE

This application is a continuation-in-part of U.S. patent application Ser. No. 08/617,537 filed Mar. 15, 1996 entitled Carbon Dioxide Detector, now abandoned which is a continuation-in-part of U.S. patent application Ser. No. 08/422,002 filed Apr. 12, 1995 entitled Carbon Dioxide Detector Coating now abandoned which is a continuation-in-part of U.S. patent application Ser. No. 07/919,788 filed Jul. 24, 1992 entitled COMPOSITION AND METHOD FOR DETECTING VAPOR AND LIQUID REACTANTS, now U.S. Pat. No. 5,322,797 which is a continuation of U.S. patent application Ser. No. 07/534,198 filed Jun. 6, 1990 entitled COMPOSITION AND METHOD FOR DETECTING VAPOR AND LIQUID REACTANTS, now U.S. Pat. No. 5,183,763.

FIELD OF THE INVENTION

The present invention relates generally to the field of chemical agent detection. More particularly, the present invention provides a method and apparatus for visually and/or colorimetrically monitoring carbon dioxide ($CO_2$) levels in a gas mixture.

BACKGROUND OF THE INVENTION

The detection and measurement of chemical agents has numerous applications, including industrial, military, medical, and municipal gas detection. One such application, lying in the field of biomedical instrumentation, is the identification and quantification of expired gases (as from a patient under general anesthesia). It is important for an anesthesiologist to know the concentrations of certain gaseous compounds (including carbon dioxide) in the surgical patient's expired airstream. This is due to the fact that the concentrations in the airstream at the end of the exhaled breath (end-tidal) are indicative of their concentrations in the blood.

Because of the rapidly changing carbon dioxide concentration in an exhaled breath stream, a suitable detector must be almost instantaneously reversible and have a rapid response.

SUMMARY OF THE INVENTION

Accordingly, the present invention provides methods and apparatus related to use of a reversible color detector to rapidly identify the presence and concentration of electrophiles, such as carbon dioxide ($CO_2$) gas, in gas mixtures at levels of approximately 1% to 5% and higher. The carbon dioxide detection involves a substantially instantaneous and reversible color change (that is, a color change occurring in less than 1 second) of a primed substrate that has been coated with a coating composition. For example, if a coated primed substrate detector is positioned in an endotracheal tube during surgery, carbon dioxide in the exhaled breath instantaneously turns the detector progressively from green-blue to shades of lighter green to yellow, while inhalation substantially reverses the color change to return the detector to green-blue.

The coating composition of the present invention comprises an effective amount of organic binder, a color indicator, an activator, a humectant, and an effective amount of filler/pigment. The organic binder comprises ethyl cellulose and the filler/pigment comprises calcium carbonate and amorphous silica. The color indicator preferably comprises bromothymol blue and bromothymol purple (preferably in about a 2:1 ratio). Significant deviation from the 2:1 ratio results in reduced sensitivity to carbon dioxide, reduced intensity of color changes and/or decreased reproducibility of color change in the presence of carbon dioxide. The activator comprises ether amine, preferably dodecyl ether amine and/or tetradecyl ether amine. No other primary or secondary alkyl amine or aromatic amine tested provided sufficient color variance with exposure to changing concentrations of carbon dioxide, combined with reversal of color change when the carbon dioxide was removed. Applying this coating composition to a primed substrate such as to the indicator substrate described herein below, or to (commercially available) pH Hydrion paper (which, when so coated, responds to gaseous carbon dioxide in a manner similar to that of a coated indicator substrate), allows detection of electrophiles of the class comprising carbon dioxide by color change of the coated primed substrate. Accordingly, the method for detecting electrophiles of the class comprising carbon dioxide comprises the steps of coating a primed substrate with a coating composition (as described herein) and sensing a color change of the coated primed substrate. Thus, a coated primed substrate provides a detector apparatus for detecting gaseous electrophiles of the class comprising carbon dioxide.

The coating composition of the present invention may be made by dissolving ethyl cellulose (binder) in acetone and then, in a high speed/high shear mixer, adding to this solution the color indicator, activator, humectant and filler/pigment. Grinding and blending in the mixer preferably continues until the composition is substantially homogeneous. The resulting coating composition is thereafter preferably stored in a closed container and protected from direct sunlight and evaporation of water until ready for application to a primed substrate. A coated primed substrate (as described above) is dried as described below, whereupon it becomes sensitive to carbon dioxide.

The rapid, reversible and quantitative response of detectors of the present invention to carbon dioxide results from the combination of a layer of dyes and indicators (the coating composition) applied over a primed substrate. The substrate is primed with a different set of dyes and the result is a synergism between the primed substrate and the coating composition that provides the desired color changes in the presence of varying concentrations of carbon dioxide gas. Whereas certain other detectors provide a color response which is dependent on time of exposure to carbon dioxide, color response of the present detector is substantially instantaneous (with virtually no further color change after the first few seconds of exposure).

BRIEF DESCRIPTION OF THE DRAWING

The drawing schematically illustrates a coated primed substrate carbon dioxide detector comprising primed substrate and coating composition.

DETAILED DESCRIPTION

The composition-coated primed substrate of the present invention may be used for detecting concentrations of carbon dioxide in a gas mixture, such as in a surgical patient's expired airstream, by sensing any color change of the coated primed substrate either visually or with appropriate instrumentation. The degree of color change of the coated primed substrate (as visually estimated or quantified by measurement) is indicative of the concentration of carbon dioxide contacting the coated primed substrate. Further, color change of the coated primed substrate is reversible and can be measured with reference to standard litmus color guides or by appropriate instrumentation such as photodetection apparatus.

For anesthesia-related applications, coated primed substrate of the present invention is preferably sensitive to gaseous carbon dioxide at concentrations from 0% to 5%, exhibiting a detectable color variation or change at distinct increments of carbon dioxide concentration within this range. The range of 0% to 5% carbon dioxide is clinically useful for persons such as anesthesiologists in evaluating the respiratory status of patients. Rapid clinical response is facilitated by the use of ethyl cellulose as the preferred binder because it provides the desired degree of permeability and receptivity to gases such as carbon dioxide.

The coating composition of the present invention comprises an organic binder, such as ethyl cellulose, a carbon dioxide ($CO_2$) sensitive color indicator preferably comprising bromothymol blue and bromothymol purple (preferably in the empirically-derived ratio of 2:1, as noted above), an activator such as an ether amine, a humectant (with water) and a filler/pigment such as calcium carbonate and amorphous silica. The present invention utilizes a basic paint technology disclosed in U.S. Pat. No. 5,183,763 issued Feb. 2, 1993, entitled COMPOSITION AND METHOD FOR DETECTING VAPOR AND LIQUID REACTANTS, which is incorporated herein by reference. The '763 patent, however, describes a composition for the detection of nucleophiles, such as ammonia and amines, whereas the present invention is directed to the detection of electrophiles, including carbon dioxide. When the coating composition of the present invention is applied to a primed substrate and dried, the coated primed substrate undergoes a distinctive and immediate color change from green-blue to yellow on exposure to carbon dioxide at concentrations of approximately 1% to 5% (as required for anesthesia-related applications), with an immediate reversal to green-blue again when carbon dioxide exposure ends. The degree of color change is repeatably indicative of $CO_2$ concentration. Note that the colors described herein are related to the partial pressure of carbon dioxide corresponding to the respective percent concentrations at approximately sea level.

The following example is presented to describe a preferred embodiment of the coating composition in a more detailed manner.

EXAMPLE 1

| Ingredients | Amount |
| --- | --- |
| Ethyl Cellulose | 8 grams |
| Acetone | 100 grams |
| Bromothymol Blue | .08 grams |
| Bromothymol Purple | .04 grams |
| Ether Amine | 20 drops |
| ($C_{12}$–$C_{16}$ ether amine) | (.7 grams) |
| Calcium Carbonate | 2 grams |
| Amorphous Silica | 2 grams |
| Sodium Sulfate Decahydrate | 2 grams |
| Polyethylene Glycol 600 | 2 grams |
| Water | 0.5 grams |

The above embodiment of coating composition is made by blending the ethyl cellulose and acetone (solvent) thoroughly until the former is dissolved and then, in a high speed/high shear mixer, adding the remaining ingredients and grinding or blending thoroughly until the composition is substantially homogeneous. The amount of acetone or other inert solvent may be varied as necessary to dissolve the ethyl cellulose because any excess solvent will evaporate during the subsequent drying step. Until used to coat a primed substrate, the substantially homogeneous coating composition should be stored in a closed container, protected from direct sunlight and from evaporation of water.

A primed substrate comprises a porous absorbent substrate of pH neutral material (such as, for example, filter paper) to which is applied (as by spraying, dipping or painting) a plurality of pH sensitive dyes. An example of a primed substrate is commercially available pH Hydrion paper which behaves in a manner similar to the indicator substrate described below when coated with the coating composition described herein.

An indicator substrate may be prepared by soaking a porous absorbent substrate (comprising, for example, an absorbent matrix such as filter paper) in an indicator solution and then drying the substrate (paper, for example). An indicator solution comprises an inert solvent and a dye component. About 50% by weight of a preferred formulation of the indicator solution dye component comprises N-methyl-4-(phenylazo)benzenamine, with the remainder (about 50% by weight) of the dye component comprising approximately equal parts by weight of the following dyes:

o-cresolsulfonephthalein (Cresol-Red)

thymolsulfonaphthalein (Thymol-Blue)

p-benzenesulfonic-azo-dimethylaniline (Methyl-Orange)

o-carboxybenzene-azo-dimethylaniline (Methyl-Red)

amino-dimethyl amino-toluphenazonium chloride (Neutral-Red)

benzene-azo-dimethyl-amine (Methyl-Yellow)

2,4,6-trinitrophenyl-methyl-nitro amine p-nitro benzene-azo-salicylic acid (Alizarin-Yellow)

thymolphthalein

A preferred indicator solution solvent comprises about equal parts by volume of acetone, ethanol, diethyl ether and acetonitrile. Other inert solvents well known to those skilled in the art would also be acceptable. If a quantity of indicator solution dye component is dissolved in the above indicator solution solvent (at about 10% concentration), the resulting indicator solution may then be used to saturate an absorbent matrix, such as a piece of filter paper, by dipping. Subsequent air-drying at room temperature and then oven-baking at about 200 degrees F drives off the remaining solvent from the filter paper to yield an indicator substrate.

A primed substrate (either the indicator substrate or pH Hydrion paper with similar characteristics as described above, for example) is then coated with the coating composition (as by painting, spray application or short contact immersion) followed by air drying. The presence of dried coating composition on the primed substrate provides a coated primed substrate which functions synergistically as a detector, the color of which is a function of gaseous carbon dioxide concentration in contact with the detector. Note that the coating composition itself does not function as a rapid-response, reversible and quantitative indicator of gaseous carbon dioxide concentration; it will only function in that manner (that is, like the detector of the present invention) when the coating composition is applied to a primed substrate as described above to form a coated primed substrate.

It has been found that sensitivity to carbon dioxide concentration decreases with time as the coated primed substrate is exposed to atmospheric $CO_2$ and as a portion of the reagents in the coating composition distill, sublime, or evaporate into the atmosphere. Further, it has been found desirable in certain applications to stabilize the coating composition by the addition of persistent humectants, and also to store coated primed substrate in closed, carbon dioxide-free containers until ready for use.

The persistent humectant preferably utilized in the present invention comprises a hydrated salt or mineral such as sodium sulfate decahydrate or aluminum sulfate octadecahydrate, a polyglycol such as polyethylene glycol 600, and water. The value of the humectant is due to the fact that the coated primed substrate is most responsive if all components are ionized or ionizable. At an ambient humidity of about 50%, coated primed substrate prepared as described herein has a useful life of approximately 24 to 48 hours before drying out to the point at which sensitivity and/or accuracy are substantially degraded. Thus, each coated primed substrate should preferably be discarded approximately 24 hours after exposure to the ambient environment and replaced with a fresh coated primed substrate.

In a test, the coating composition described in Example 1 above was applied to pH Hydrion paper as well as to the indicator substrate described herein, and each coated primed substrate was exposed to varied concentrations of carbon dioxide. Upon exposure to the varied concentrations of carbon dioxide, each coated primed substrate exhibited definite and reproducible bands of color representing each carbon dioxide concentration. The color changes observed are identified in Table 1 below.

TABLE 1

| % $CO_2$ (in air) | Color |
|---|---|
| 0% | Dark Green-Blue |
| 1% | Teal, Dark Green with Blue highlight |
| 2% | Dark Green (Ivy) |
| 3% | Light Green |
| 4% | Chartreuse (Yellow-Green) |
| 5% | Lemon Yellow |
| 10% | Orange Yellow |

All color changes persisted only during exposure to carbon dioxide and, upon venting or removal of the carbon dioxide, the color reversed almost immediately to its original state. The color change identified in Table 1 above thus provides a reproducible measurement of carbon dioxide concentration which can be estimated visually or quantified using photo-optical (colorimetric) techniques well known to those skilled in the art.

It is to be understood that the present invention includes novel methods and combinations of materials, such as the components of the coating composition (including a primary ether amine as an activator), the preparation of an indicator substrate, and the coating of an indicator substrate with coating composition. Interaction of the coating composition with the primed substrate (specifically with dye constituents thereof) produces a high degree of sensitivity and reversibility of coated-primed substrate response to exposure to $CO_2$.

Additionally, it has been found that the ethyl cellulose provides a desired combination of water insoluble binder and a highly permeable membrane to let the detected gases, such as carbon dioxide, through. That is, ethyl cellulose provides a desired vehicle for transfer of vapor to the indicator and a binder for attaching the indicator to the substrate material.

The effect of carbon dioxide concentration on color change of a coated primed substrate of the present invention appears to peak at approximately 15% $CO_2$, at which point the composition becomes a bright yellow and increased concentrations have no further visible effect.

The drawing schematically illustrates a coated primed substrate carbon dioxide detector 30 comprising primed substrate 10 and coating composition 20. A coating composition is shown substantially uniformly distributed over a substrate except for a relatively small portion of the substrate which remains uncoated. Note that the preferred manner of distributing coating composition over a substrate is generally dependent in part on the specific intended application of the detector. Relatively thin coatings may be preferred to enhance the desired interaction of coating composition and substrate, and a thickness gradient in the coating may be desirable in a detector with broad applications. Intensity of color change in a coated primed substrate detector affects ease of use and may also be a function of coating thickness. Thus, the coating schematically illustrated in the drawing is for illustrative purposes only.

While preferred embodiments of the coated primed substrate carbon dioxide detector of the present invention has been described, it is not intended to limit the invention to the particular form set forth, but on the contrary, it is intended to cover such alternatives, modifications, and equivalents as may be included within the spirit and scope of the invention as defined by the appended claims.

I claim:

1. A reversible carbon dioxide detector comprising:
   a primed substrate comprising a primer comprising a first amount of a first plurality of dyes comprising pH sensitive color indicators and an amount of moisture effective to permit said pH sensitive color indicators to interact with carbon dioxide without substantial migration or flow of said first plurality of dyes on said substrate;
   a coating over at least a portion of said substrate, said coating comprising a second amount of an effective activator, a third amount of a water insoluble organic binder, and a fourth amount of a second plurality of dyes comprising carbon dioxide sensitive color indicators;
   wherein said water insoluble binder facilitates permeation of carbon dioxide from a surrounding medium through said coating into reversible contact with a combination of said first plurality of dyes and said second plurality of dyes;
   wherein said first, second, third, and fourth amounts are effective to permit said combination of said first plurality of dyes and said second plurality of dyes to interact with said carbon dioxide to substantially instantaneously produce incremental reversible changes in color comprising a reproducible array of separate colors in which said separate colors correlate to separate given concentrations of carbon dioxide in a surrounding medium.

2. The detector of claim 1 wherein said effective activator is an ether amine selected from the group consisting of dodecyl ether amine and tetradecyl ether amine.

3. The detector of claim 1 wherein said water insoluble organic binder is ethylcellulose.

4. The detector of claim 3 wherein said second plurality of dyes is a combination of bromothymol blue and bromothymol purple at a ratio of about 2:1.

5. The detector of claim 1 wherein said second plurality of dyes is a combination of bromothymol blue and bromothymol purple at a ratio of about 2:1.

6. The detector of claim 5 further comprising a persistent humectant effective to maintain components in said coating in a form selected from the group consisting of ionized form and ionizable form.

7. The detector of claim 6 wherein said effective activator is an ether amine selected from the group consisting of dodecyl ether amine and tetradecyl ether amine.

8. The detector of claim 1 wherein said first plurality of dyes comprise N-methyl-4-(phenylazo)benzamine.

9. The detector of claim 8 further comprising a persistent humectant effective to maintain components in said coating in a form selected from the group consisting of ionized form and ionizable form.

10. The detector of claim 8 wherein said second plurality of dyes is a combination of bromothymol blue and bromothymol purple at a ratio of about 2:1.

11. The detector of claim 10 further comprising a persistent humectant effective to maintain components in said coating in a form selected from the group consisting of ionized form and ionizable form.

12. The detector of claim 10 wherein said effective activator is an ether amine selected from the group consisting of dodecyl ether amine and tetradecyl ether amine.

13. The detector of claim 8 wherein said water insoluble organic binder is ethylcellulose.

14. The detector of claim 13 wherein said second plurality of dyes is a combination of bromothymol blue and bromothymol purple at a ratio of about 2:1.

15. The detector of claim 14 wherein said effective activator is an ether amine selected from the group consisting of dodecyl ether amine and tetradecyl ether amine.

16. The detector of claim 13 further comprising a persistent humectant effective to maintain components in said coating in a form selected from the group consisting of ionized form and ionizable form.

17. The detector of claim 16 wherein said effective activator is an ether amine selected from the group consisting of dodecyl ether amine and tetradecyl ether amine.

18. A reversible carbon dioxide detector comprising:
a primed substrate comprising a primer comprising a first amount of a first plurality of dyes comprising about 50% by weight N-methyl-4-(phenylazo)benzenamine and
approximately equal parts by weight of dyes selected from the group consisting of o-cresolsulfonaphthalein; thymolsulfonaphthalein; p-benzenesulfonic-azo-dimethylaniline; o-carboxybenzene-azo-dimethylaniline; amino-dimethyl amino-toluphenazonium chloride; benzene-azo-dimethyl-amine; 2,4,6-trinitrophenyl-methyl-nitro amine; p-nitro benzene-azo-salicylic acid; and thymolphthalein, said primer further comprising an amount of moisture effective to permit said first plurality of dyes to interact with carbon dioxide without substantial migration or flow of said first plurality of dyes on said substrate;
a coating over at least a portion of said substrate, said coating comprising a second amount of an effective activator, a third amount of a water insoluble organic binder, and a fourth amount of a second plurality of dyes comprising carbon dioxide sensitive color indicators;
wherein said water insoluble binder facilitates permeation of carbon dioxide from a surrounding medium through said coating into reversible contact with a combination of said first plurality of dyes and said second plurality of dyes;
wherein said first, second, third, and fourth amounts are effective to permit said combination of said first plurality of dyes and said second plurality of dyes to interact with said carbon dioxide to substantially instantaneously produce incremental reversible changes in color comprising a reproducible array of separate colors in which said separate colors correlate to separate given concentrations of carbon dioxide in a surrounding medium.

19. The detector of claim 18 wherein said second dye is a combination of bromothymol blue and bromothymol purple at a ratio of about 2:1.

20. The detector of claim 19 wherein said effective activator is an ether amine selected from the group consisting of dodecyl ether amine and tetradecyl ether amine.

21. The detector of claim 18 wherein said water insoluble organic binder is ethylcellulose.

22. The detector of claim 21 wherein said second dye is a combination of bromothymol blue and bromothymol purple at a ratio of about 2:1.

23. The detector of claim 21 wherein said effective activator is an ether amine selected from the group consisting of dodecyl ether amine and tetradecyl ether amine.

24. A reversible carbon dioxide detector comprising:
a primed substrate comprising a primer comprising a first amount of a first plurality of dyes comprising pH sensitive color indicators and an amount of moisture effective to permit said pH sensitive color indicators to interact with carbon dioxide without substantial migration or flow of said first plurality of dyes on said substrate;
a coating over at least a portion of said substrate, said coating comprising:
a second amount of an effective activator;
a third amount of a water insoluble organic binder,
a fourth amount of a second plurality of dyes comprising carbon dioxide sensitive color indicators; and,
a fifth amount of a persistant humectant effective to maintain components in said coating in a form selected from the group consisting of ionized form and ionizable form;
wherein said water insoluble binder facilitates permeation of carbon dioxide from a surrounding medium through said coating into reversible contact with a combination of said first plurality of dyes and said second plurality of dyes;
wherein said first, second, third, fourth, and fifth amounts are effective to permit said combination of said first plurality of dyes and said second plurality of dyes to interact with said carbon dioxide to substantially instantaneously produce incremental reversible changes in color comprising a reproducible array of separate colors in which said separate colors correlate to separate given concentrations of carbon dioxide in a surrounding medium.

25. The detector of claim 24 wherein said second plurality of dyes is a combination of bromothymol blue and bromothymol purple at a ratio of about 2:1.

26. The detector of claim 24 wherein said water insoluble organic binder is ethylcellulose.

27. The detector of claim 26 wherein said second plurality of dyes is a combination of bromothymol blue and bromothymol purple at a ratio of about 2:1.

28. The detector of claim 24 wherein said first plurality of dyes comprise about 50% by weight of said N-methyl-4-(phenylazo)benzenamine; and approximately equal parts by weight of dyes selected from the group consisting of o-cresolsulfonephthalein; thymolsulfonaphthalein; p-benzenesulfonic-azo-dimethylaniline; o-carboxybenzeneazo-dimethylaniline; amino-dimethyl amino-toluphenazonium chloride; benzene-azo-dimethyl-amine; 2,4,6-trinitrophenyl-methyl-nitro amine; p-nitro benzene-azo-salicylic acid; and thymolphthalein.

29. The detector of claim 28 wherein said second plurality of dyes is a combination of bromothymol blue and bromothymol purple at a ratio of about 2:1.

30. The detector of claim 28 wherein said water insoluble organic binder is ethylcellulose.

31. The detector of claim 30 wherein said second plurality of dyes is a combination of bromothymol blue and bromothymol purple at a ratio of about 2:1.

\* \* \* \* \*